United States Patent
Chaturvedi et al.

(10) Patent No.: US 11,992,235 B2
(45) Date of Patent: May 28, 2024

(54) SYSTEM TO DIFFERENTIATE AND IDENTIFY TYPES OF TISSUE WITHIN A REGION PROXIMATE TO A WORKING END OF A SURGICAL INSTRUMENT

(71) Applicant: Briteseed, LLC, Chicago, IL (US)

(72) Inventors: Amal Chaturvedi, Chicago, IL (US); Hariharan Subramanian, Mundelein, IL (US); Jonathan Gunn, Chicago, IL (US); Shetha Shukair, Chicago, IL (US); Paul Le Rolland, Chicago, IL (US)

(73) Assignee: Briteseed, LLC, Chicago, IL (US)

( * ) Notice: Subject to any disclaimer, the term of this patent is extended or adjusted under 35 U.S.C. 154(b) by 314 days.

(21) Appl. No.: 16/077,041

(22) PCT Filed: Feb. 10, 2017

(86) PCT No.: PCT/US2017/017436
§ 371 (c)(1),
(2) Date: Aug. 9, 2018

(87) PCT Pub. No.: WO2017/139624
PCT Pub. Date: Aug. 17, 2017

(65) Prior Publication Data
US 2019/0046220 A1    Feb. 14, 2019

Related U.S. Application Data

(60) Provisional application No. 62/294,996, filed on Feb. 12, 2016.

(51) Int. Cl.
*A61B 17/29*    (2006.01)
*A61B 5/00*    (2006.01)
(Continued)

(52) U.S. Cl.
CPC .......... *A61B 17/29* (2013.01); *A61B 5/02416* (2013.01); *A61B 5/1076* (2013.01);
(Continued)

(58) Field of Classification Search
CPC .............. A61B 1/00013; A61B 5/0873; A61B 2034/2055; A61B 5/1455; A61B 1/00163;
(Continued)

(56) References Cited

U.S. PATENT DOCUMENTS 5,129,400 A    7/1992    Makino et al.
5,259,761 A    11/1993   Schnettler et al.
(Continued)

FOREIGN PATENT DOCUMENTS

EP    2 353 534    8/2011
GB    1 445 678    8/1976
(Continued)

OTHER PUBLICATIONS

Li et al. 2006 Optic Express 14:7841-7851 (Year: 2006).*
(Continued)

*Primary Examiner* — Keith M Raymond
*Assistant Examiner* — Patrick M Mehl
(74) *Attorney, Agent, or Firm* — Cook Alex Ltd.

(57) ABSTRACT

A surgical system used to determine the presence of a vessel within a region (102) proximate to a working end (104) of a surgical instrument (106) includes at least one light emitter (110) disposed at the working end (104) of the surgical instrument (106), and at least one light sensor (112) disposed at the working end (104) of the surgical instrument (106) and configured to receive light emitted from the at least one light emitter (110) and reflected from the region (102), the at least one light sensor (112) adapted to generate a signal comprising a first pulsatile component and a second non-pulsatile component. The system also includes a controller (114)
(Continued)

coupled to the at least one light sensor (112), the controller (114) comprising a splitter (116) to separate the first pulsatile component from the second non-pulsatile component and an analyzer (118) to determine the presence of the vessel within the region (102) proximate to the working end (104) of the surgical instrument (106) based on the first pulsatile component.

19 Claims, 9 Drawing Sheets

(51) Int. Cl.
```
A61B 5/024      (2006.01)
A61B 5/107      (2006.01)
A61B 17/00      (2006.01)
A61B 17/072     (2006.01)
A61B 17/128     (2006.01)
A61B 17/32      (2006.01)
A61B 18/08      (2006.01)
A61B 90/00      (2016.01)
```
(52) U.S. Cl.
CPC .... *A61B 5/489* (2013.01); *A61B 2017/00057* (2013.01); *A61B 2017/00115* (2013.01); *A61B 2017/07214* (2013.01); *A61B 17/1285* (2013.01); *A61B 2017/2926* (2013.01); *A61B 2017/320044* (2013.01); *A61B 18/085* (2013.01); *A61B 2090/0807* (2016.02); *A61B 2505/05* (2013.01)

(58) Field of Classification Search
CPC .... A61B 2562/0238; A61B 2562/0242; A61B 8/0891; A61B 5/02416; A61B 5/0261; A61B 5/02154; A61B 5/02; A61B 5/021; A61B 5/026; A61B 17/29; A61B 5/1076; A61B 5/489; A61B 17/1285; A61B 5/0205; A61B 5/024; A61B 2562/146; A61B 5/0066; A61H 2230/25; G06T 2207/30004; G06T 2207/30101
See application file for complete search history.

(56) References Cited

U.S. PATENT DOCUMENTS

| | | |
|---|---|---|
| 5,762,609 A | 6/1998 | Benaron et al. |
| 5,769,791 A | 6/1998 | Benaron et al. |
| 5,772,597 A | 6/1998 | Goldberger et al. |
| 5,785,658 A * | 7/1998 | Benaron ............... A61B 5/0086 600/473 |
| 5,807,261 A | 9/1998 | Benaron et al. |
| 5,987,346 A | 11/1999 | Benaron et al. |
| 6,178,340 B1 | 1/2001 | Svetliza |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,838,210 B2 | 9/2014 | Wood et al. |
| 9,114,226 B1 | 8/2015 | Lash et al. |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0111085 A1 | 6/2004 | Singh |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0155194 A1 | 7/2006 | Marcotte et al. |
| 2007/0038118 A1 | 2/2007 | DePue et al. |
| 2009/0018414 A1 | 1/2009 | Toofan |
| 2009/0054908 A1 | 2/2009 | Zand et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0105812 A1* | 5/2012 | Dekker ............... H04N 9/3129 353/31 |
| 2012/0143182 A1 | 6/2012 | Ullrich et al. |
| 2012/0172842 A1 | 7/2012 | Sela et al. |
| 2012/0179011 A1 | 7/2012 | Moon et al. |
| 2012/0296205 A1 | 11/2012 | Chernov et al. |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0016132 A1* | 1/2014 | Schmitz ............ G01N 33/4833 356/337 |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0236019 A1 | 8/2014 | Rahum |
| 2014/0276088 A1 | 9/2014 | Drucker |
| 2014/0303437 A1* | 10/2014 | Kikuchi ............... A61B 34/20 600/106 |
| 2014/0313482 A1 | 10/2014 | Shahidi et al. |
| 2015/0011896 A1 | 1/2015 | Yelin et al. |
| 2015/0051460 A1 | 2/2015 | Saxena et al. |
| 2015/0057511 A1* | 2/2015 | Basu ................. A61B 5/02433 600/323 |
| 2015/0066000 A1 | 3/2015 | An et al. |
| 2015/0223694 A1* | 8/2015 | Funane ............... A61B 5/1455 600/407 |
| 2017/0181701 A1 | 6/2017 | Fehrenbacher et al. |
| 2017/0367580 A1* | 12/2017 | DiMaio ............... A61B 5/445 |

(56) References Cited

U.S. PATENT DOCUMENTS

| | | | |
|---|---|---|---|
| 2018/0042522 | A1 | 2/2018 | Subramanian et al. |
| 2018/0098705 | A1 | 4/2018 | Chaturvedi et al. |

FOREIGN PATENT DOCUMENTS

| | | | | |
|---|---|---|---|---|
| JP | H10-005245 | | 1/1998 | |
| JP | 2003-019116 | | 1/2003 | |
| JP | 2010-081972 | | 4/2010 | |
| JP | 2012-152493 | | 8/2012 | |
| JP | 2014-087387 | | 5/2014 | |
| JP | 2014-132992 | | 7/2014 | |
| JP | 2015-502197 | | 1/2015 | |
| WO | WO98/27865 | | 7/1998 | |
| WO | WO2001/060427 | | 8/2001 | |
| WO | WO03/039326 | | 5/2003 | |
| WO | WO2004/030527 | | 4/2004 | |
| WO | WO2005/091978 | | 10/2005 | |
| WO | WO2008/082992 | | 7/2008 | |
| WO | WO2009/144653 | | 12/2009 | |
| WO | WO2011/013132 | | 2/2011 | |
| WO | WO2011013132 | A1 * | 2/2011 | ............... A61B 5/00 |
| WO | WO2012/158774 | | 11/2012 | |
| WO | WO2013/134411 | | 9/2013 | |
| WO | WO2013134411 | A1 * | 9/2013 | ............. A61B 17/29 |
| WO | WO2014/194317 | | 12/2014 | |
| WO | WO2015/148504 | | 10/2015 | |
| WO | WO2016/134327 | | 8/2016 | |
| WO | WO2016/134330 | | 8/2016 | |
| WO | WO2017/062720 | | 4/2017 | |
| WO | WO2017/139642 | | 8/2017 | |
| WO | WO2018/044722 | | 3/2018 | |

OTHER PUBLICATIONS

Ci et al. 1999 Applied Spectrosc. 53:312-5 (Year: 1999).*
Narasimha-Iyer et al. 2007 IEEE Transactions on Biomedical Engineering 54:1427-1435 (Year: 2007).*
Lopez Doc No. AN4327 Pulse Oximeter Fundamentals and Design—Freescale Semiconductor INC 99pages (Year: 2011).*
Thatcher et al. 2016 Advances in Wound Care 5 360-378 (Year: 2016).*
International Search Report and Written Opinion, counterpart PCT application PCT/US2017/017436, 15 pages (dated May 19, 2017).
Akl et al., Performance Assessment of an Opto-Fluidic Phantom Mimicking Porcine Liver Parenchyma, J. Bio. Optics, vol. 17(7) 077008-1 to 077008-9 (Jul. 2012).
Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).
Figueiras et al., Self-Mixing Microprobe for Monitoring Microvascular Perfusion in Rat Brain, Med. Bio. Eng'r Computing 51:103-112 (Oct. 12, 2012).
Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).
Ibey et al., Processing of Pulse Oximeter Signals Using Adaptive Filtering and Autocorrelation to Isolate Perfusion and Oxygenation Components, Proc SPIE, vol. 5702, 54-60 (2005).
Li et al., Pulsation-Resolved Deep Tissue Dynamics Measured with Diffusing-Wave Spectroscopy, Optics Express, vol. 14, No. 17, 7841-7851 (Aug. 21, 2006).
Mendelson et al., In-vitro Evaluation of a Dual Oxygen Saturation/Hematocrit Intravascular Fiberoptic Catheter, Biomed Instrum. Technol. 24(3):199-206 (May/Jun. 1990).
Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).
Subramanian, Real Time Perfusion and Oxygenation Monitoring in an Implantable Optical Sensor, Thesis Texas A&M Univ. (Dec. 2004).
Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).
Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).
Japanese Search Report with English translation, counterpart Japanese App. No. 2018-542207 (dated Jan. 15, 2021) (29 pages).
Notice of Reasons for Refusal with English translation, counterpart Japanese App. No. 2018-542207 (dated Jan. 26, 2021) (6 pages).

* cited by examiner

SYSTEM TO DIFFERENTIATE AND IDENTIFY TYPES OF TISSUE WITHIN A REGION PROXIMATE TO A WORKING END OF A SURGICAL INSTRUMENT

The present application is a U.S. National Stage of PCT International Patent Application No. PCT/US2017/017436, filed Feb. 10, 2017, which claims the benefit of U.S. Provisional Application No. 62/294,996, filed Feb. 12, 2016, both of which are hereby incorporated herein by reference.

BACKGROUND

This patent is directed to a system and method for determining the characteristics of a tissue, and in particular to a system and method using reflected light that includes a non-pulsating component and a pulsating component.

Systems and methods that identify artifacts, and in particular vessels, in the surgical field during a surgical procedure provide valuable information to the surgeon or surgical team. In general terms, U.S. hospitals lose billions of dollars annually in unreimbursable costs because of inadvertent vascular damage during surgery. The involved patients face a mortality rate of up to 32%, and likely will require corrective procedures and remain in the hospital for an additional nine days, resulting in tens, if not hundreds, of thousands of dollars in added costs of care. Consequently, there is this significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally-invasive surgical procedures. Traditionally, surgeons have relied upon tactile sensation during surgical procedures both to identify blood vessels and to avoid inadvertent damage to these vessels. Because of the shift towards minimally-invasive procedures, including laparoscopic and robotic surgeries, surgeons have lost the ability to use direct visualization and the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity).

While the ability to determine the presence or absence of a vessel within the surgical field provides valuable advantages to the surgeon or surgical team and is of particular importance for minimally-invasive procedures where direct visualization and tactile methods of identification have been lost, the ability not simply to detect, but also to characterize, the identified vasculature provides additional important advantages. For example, it would be advantageous to provide information relating to the size of the vessel, such as the inner or outer diameter of the vessel. Size information is particular relevant as the Food and Drug Administration presently approves, for example, thermal ligature devices to seal and cut vessels within a given size range, typically less than 7 mm in diameter for most thermal ligature devices. If a thermal ligature device is used to seal a larger blood vessel, then the failure rate for a seal thus formed may be as high as 19%.

Further, it would be of assistance to be able to determine the type of tissue surrounding the vessel, not simply that the vessel is surrounded by tissue. Characterization of the non-vascular tissue, such as its depth overlying a detected vessel, would provide still further advantages.

In addition, it would be preferable to provide this information with minimal delay between vessel or tissue detection and analysis, such that the information may be characterized as real-time or near real-time (e.g., <2 seconds). If considerable time is required for analysis, then at a minimum this delay will increase the time required to perform the procedure. In addition, the delay may increase surgeon fatigue, because the surgeon will be required to move at a deliberate pace to compensate for the delay between motion of the instrument and delivery of the information. Such delays may in fact hinder adoption of the system, even if the information provided reduces the risk of vascular injury.

Further, it would be advantageous to detect and analyze the vasculature and other tissues without the need to use a contrast medium or agent. While the use of a contrast agent to identify vasculature has become conventional, the use of the agent still adds to the complexity of the procedure. The use of the agent may require additional equipment that would not otherwise be required, and increase the medical waste generated by the procedure. Further, the use of the contrast agent adds a risk of adverse reaction by the patient.

As set forth in more detail below, the present disclosure describes a surgical system including a system and method for tissue characteristics, such as vessel presence, vessel size, tissue type, and tissue depth, embodying advantageous alternatives to the existing methods, which may provide for improved identification for avoidance or isolation of tissues.

SUMMARY

According to an aspect of the present disclosure, a surgical system used to determine the presence of a vessel within a region proximate to a working end of a surgical instrument includes at least one light emitter disposed at the working end of the surgical instrument, and at least one light sensor disposed at the working end of the surgical instrument and configured to receive light emitted from the at least one light emitter and reflected from the region, the at least one light sensor adapted to generate a signal comprising a first pulsatile component and a second non-pulsatile component. The system also includes a controller coupled to the at least one light sensor, the controller comprising a splitter to separate the first pulsatile component from the second non-pulsatile component and an analyzer to determine the presence of the vessel within the region proximate to the working end of the surgical instrument based on the first pulsatile component.

According to another aspect of the present disclosure, a method of determining the presence of a vessel within a region proximate to a working end of a surgical instrument includes emitting light at the working end of the surgical instrument in the direction of the region, sensing light reflected from the region at the working end of the surgical instrument, generating a signal having a first pulsatile component and a second non-pulsatile component based on the light sensed at the working end of the surgical instrument, and determining the presence of the vessel within the region proximate to the working end of the surgical instrument based on the first pulsatile component of the signal.

According to a further aspect of the present disclosure, a surgical system used to differentiate between types of tissue within a region proximate to a working end of a surgical instrument includes at least one light emitter disposed at the working end of the surgical instrument, and at least one light sensor disposed at the working end of the surgical instrument and configured to receive light emitted from the at least one light emitter and reflected from the region, the at least one light sensor adapted to generate a signal comprising a first pulsatile component and a second non-pulsatile component. The system also includes a controller coupled to the at least one light sensor, the controller comprising a splitter to separate the first pulsatile component from the second non-pulsatile component and an analyzer to differentiate between types of tissue within the region proximate to the working end of the surgical instrument based on the second non-pulsatile component.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

Figure 1:
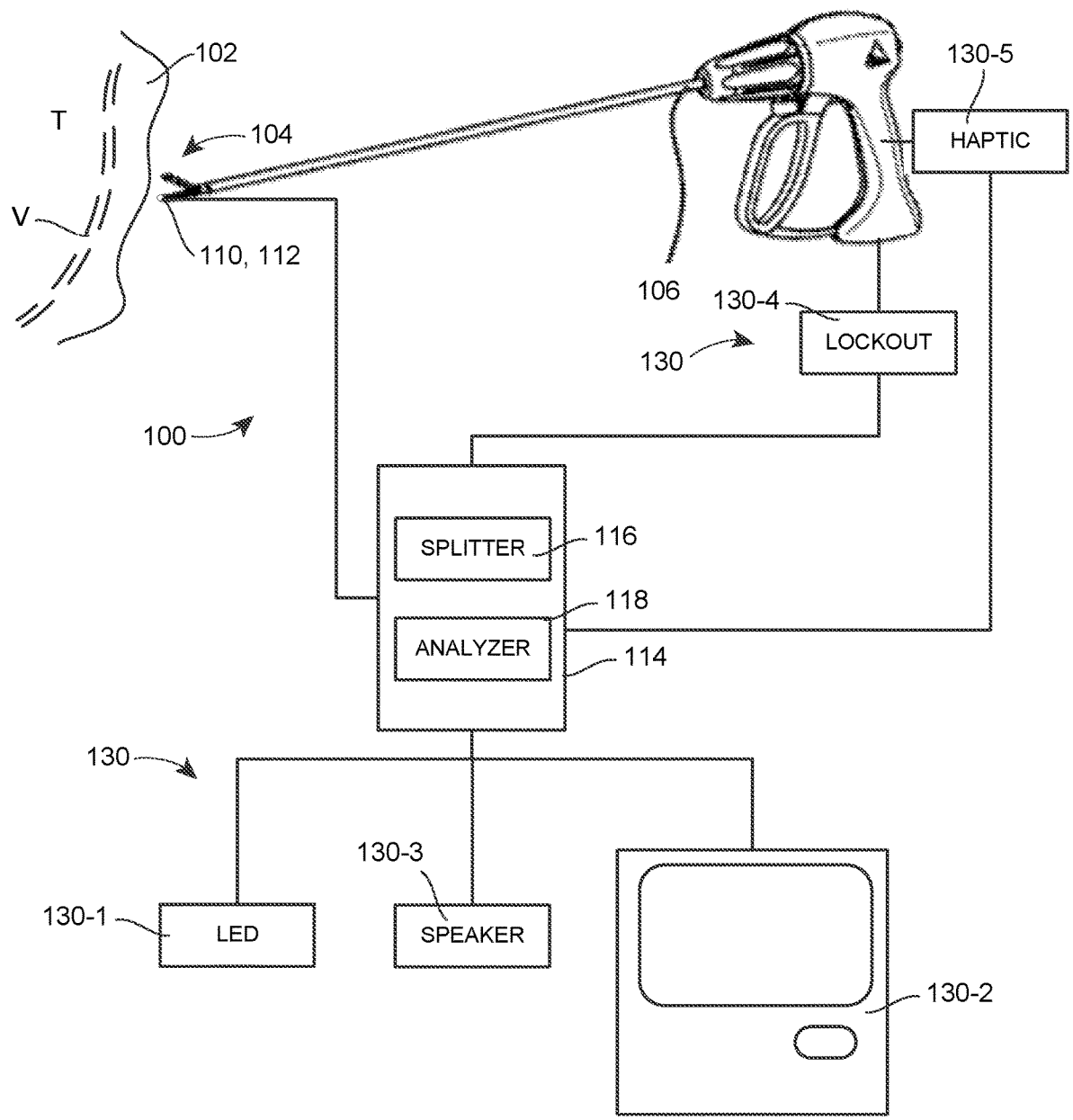
FIG. 1 is a schematic diagram of a surgical system according to an embodiment of the present disclosure.

A surgical system according to an embodiment of the present disclosure includes at least one light emitter, at least one light sensor, and a controller. The system may also include a surgical instrument as well.

The system may be used to determine the presence of a vessel within a region proximate to a working end of the surgical instrument. In particular, it is believed that the system may be used to determine the presence of a vessel within the region proximate to the working end of the surgical instrument regardless of the presence or the type of tissue surrounding the vessel. The embodiments of the system described below perform determinations relative to the presence of the vessel within the targeted region based on the reflected light as determined by the light sensor. According to other embodiments, it may be possible to determine characteristics of the vessel, or to determine if other types of tissue (other than vessels) are present and to differentiate between the different tissue types.

FIGS. 1-5 illustrate an embodiment of such a surgical system 100 used to determine the presence of a vessel, V, disposed within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIGS. 1 and 2 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue and/or liver tissue.

The surgical system 100 includes at least one light emitter 110 (or simply the light emitter 110), at least one light sensor or detector 112 (or simply the light sensor 112), and a controller 114 coupled to the light emitter 110 and the light sensor 112. As noted above, the system 100 also may include the surgical instrument 106.

Figure 2:
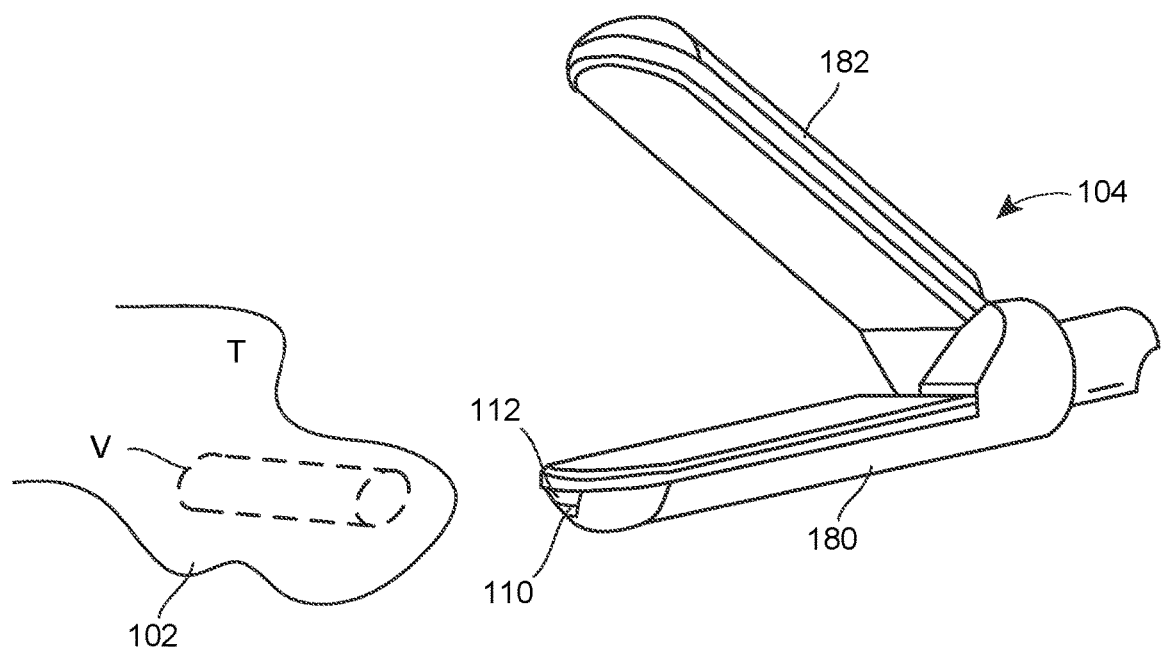
FIG. 2 is an enlarged, fragmentary view of an embodiment of the surgical instrument with light emitter and light sensor in fixed relation to each other, with a section of a vessel illustrated as proximate the light emitter and light sensor.
Figure 3:
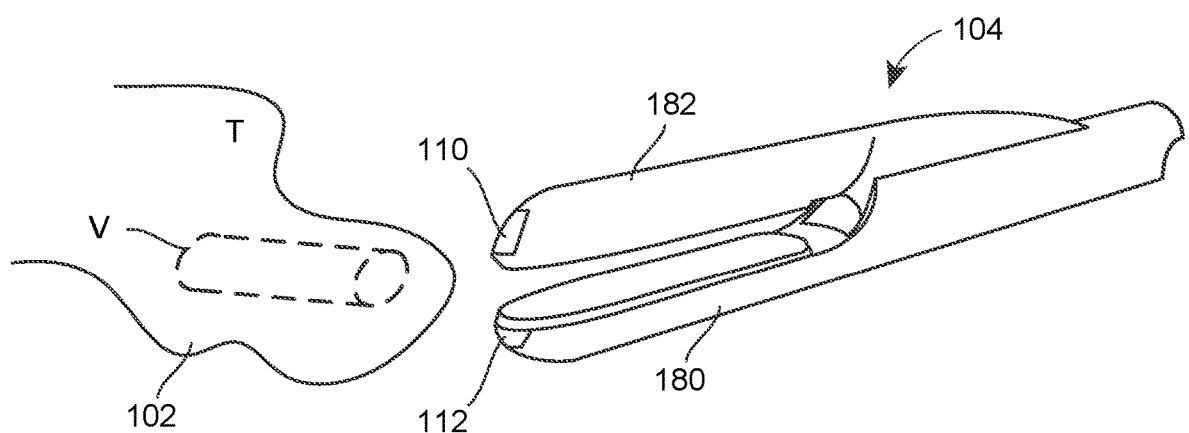
FIG. 3 is an enlarged, fragmentary view of an embodiment of a surgical instrument with light emitter and light sensor moveable relative to each other to vary the spacing therebetween, with a section of a vessel illustrated as proximate the light emitter and light sensor.
Figure 4:
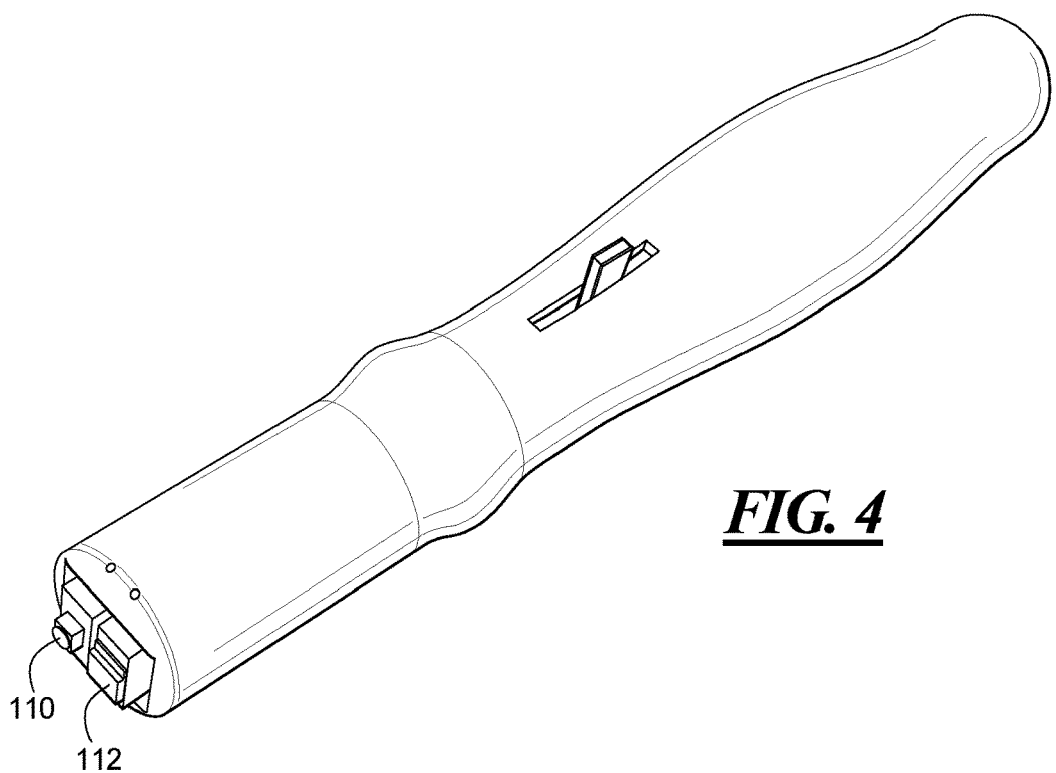
FIG. 4 is a perspective view of an embodiment of a surgical instrument with light emitter and light sensor moveable relative to each other to vary the angle of the light emitter and/or light sensor relative to a surface of the surgical instrument.
Figure 5:
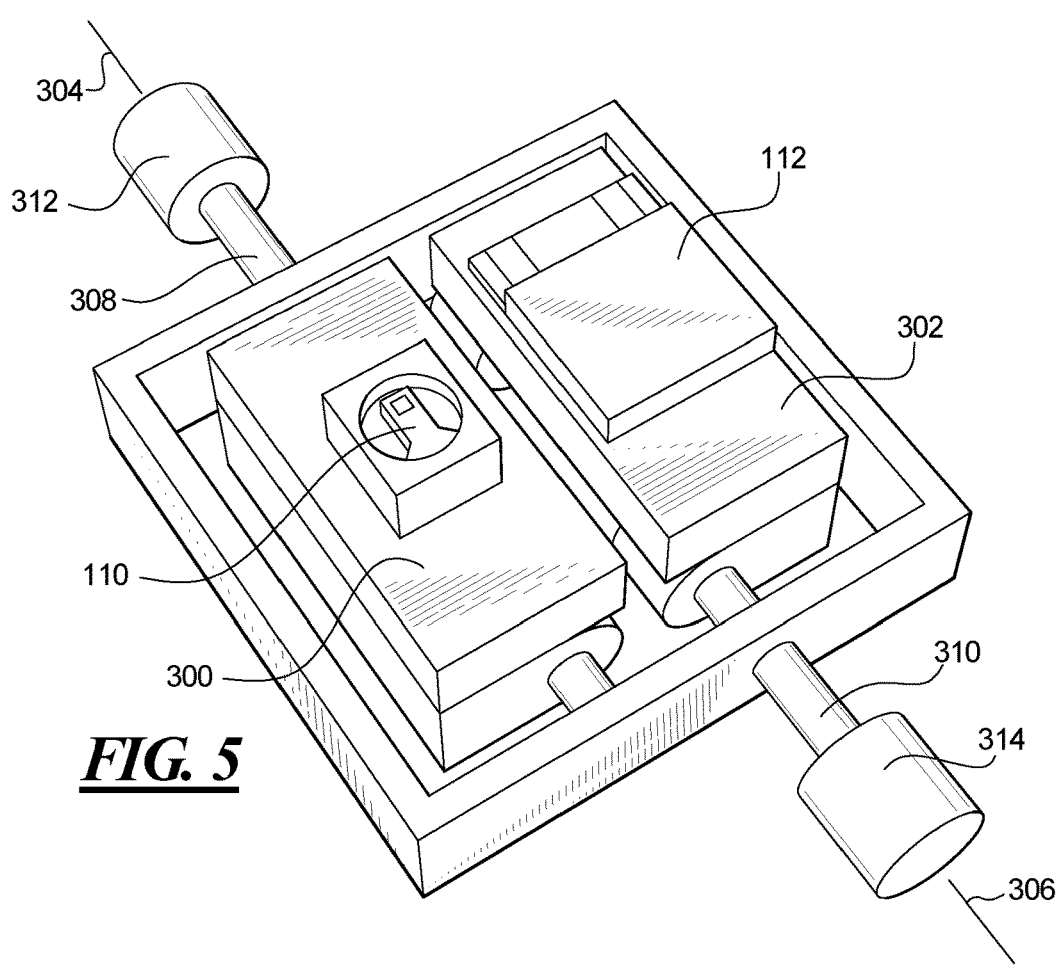
FIG. 5 is an enlarged, perspective view of the light emitter, the light sensor and the mechanism to vary the angle of the light emitter and/or light sensor relative to the surface of the surgical instrument.

The light emitter 110 is disposed at the working end 104 of the surgical instrument 106. The light sensor 112 is also disposed at the working end 104 of the surgical instrument 106. As illustrated in FIG. 2, the light emitter 110 and the light sensor 112 may be disposed in fixed relation to each other, for example on a single jaw of a two device, such as a thermal ligation device, or on a blunt end of a laparoscopic tool (e.g., a Kittner dissector or suction irrigator). Alternatively, as illustrated in FIG. 3, the light emitter 110 and the light sensor 112 may be disposed so that the spacing between the light emitter 110 and the light sensor 112 may be adjusted, for example by positioning the light emitter 110 at the end or tip of one of the jaws of a two-jaw device and the light sensor 112 at the end or tip of the other the jaws of the two-jaw device. As a further alternative, as illustrated in FIGS. 4 and 5, the light emitter 110 and/or the light sensor 112 may be disposed so that the angle between the light emitter 110 and/or light sensor 112 may be adjusted relative to a surface of the surgical instrument, for example by positioning the light emitter 110 and/or the light sensor 112 on a frame that is at a minimum adjustable about an axis.

The light emitter 110 is adapted to emit light of at least one wavelength. For example, the light emitter 110 may emit light having a wavelength of 660 nm. This may be achieved with a single element, or a plurality of elements (which elements may be arranged or configured into an array, for example, as explained in detail below). In a similar fashion, the light sensor 112 is adapted to detect light at the at least one wavelength (e.g., 660 nm). According to the embodiments described herein, the light sensor 112 also may include one or more elements, which elements may be arranged or configured into an array.

According to certain embodiments, the light emitter 110 may be configured to emit light of at least two different wavelengths, and the light sensor 112 may be configured to detect light at the at least two different wavelengths. As one example, the light emitter 110 may emit and the light sensor 112 may detect light in the visible range and light in the near-infrared or infrared range. Specifically, the light emitter 110 may emit and the light sensor 112 may detect light at 660 nm and at 910 nm. Such an embodiment may be used, for example, to ensure optimal penetration of blood vessel V and the surrounding tissue T under in vivo conditions.

It is also possible to the light emitter 110 to emit light of a plurality of different wavelengths (e.g., white light), and the light sensor 112 may be configured to detect light at one or more of the wavelengths.

Depending upon the effect of changes in blood flow, light of a third wavelength may also be emitted and sensed. That is, if the method of detection is found to be sensitive to varying rates of blood flow in the vessel of interest, light at 810 nm (i.e., at the isobestic point) may be emitted and sensed to permit normalization of the results to limit or eliminate the effects of changes in blood flow rate.

According to the embodiments of this disclosure, the individual light sensor 112 is adapted to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 112 is in the form of an array, the pulsatile and non-pulsatile information may be generated for each element of the array, or at least for each element of the array that defines the at least one row of the array.

As to the pulsatile component, it will be recognized that a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 112 will produce a signal (that is passed to the controller 114) with a particular AC waveform that corresponds to the movement of the blood through the vessel. In particular, the AC waveform corresponds to the light reflected by the pulsatile blood flow within the vessel. On the other hand, the DC component corresponds principally to light reflected and scattered by the superficial tissues.

Thus, according to the disclosed embodiments, the controller 114 is coupled to the light sensor 112, and includes a splitter 116 to separate the first pulsatile component from the second non-pulsatile component for the light sensor 112. The controller 114 also includes an analyzer 118 to determine at least the presence the vessel V within the region 102 proximate to the working end 104 of the surgical instrument 106 based on the pulsatile component. To display, indicate or otherwise convey the presence of the vessel V within the region 102, the controller 114 may be coupled to an output device or indicator 130 (see FIG. 1), which may provide a visible, audible, tactile or other signal to the user of the instrument 106.

According to certain embodiments, the splitter 116 and the analyzer 118 may be defined by one or more electrical circuit components. According to other embodiments, one or more processors (or simply, the processor) may be programmed to perform the actions of the splitter 116 and the analyzer 118. According to still further embodiments, the splitter 116 and the analyzer 118 may be defined in part by electrical circuit components and in part by a processor programmed to perform the actions of the splitter 116 and the analyzer 118.

For example, the splitter 116 may include or be defined by the processor programmed to separate the first pulsatile component from the second non-pulsatile component. Further, the analyzer 118 may include or be defined by the processor programmed to determine the presence of (or to quantify the size of) the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

Figure 6:
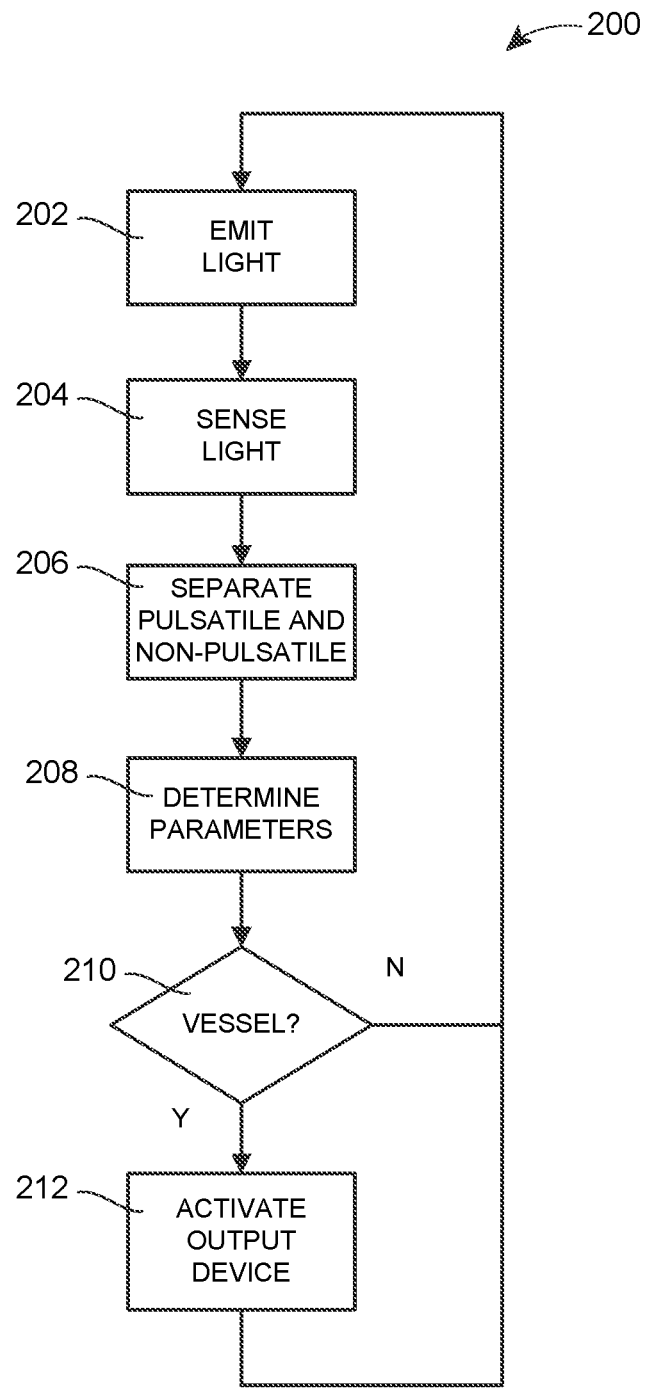
FIG. 6 is a flowchart of an embodiment of a method of operating the surgical system of FIG. 1.

In addition to the system 100, a method 200 of determining if the presence of a vessel V within a region 102 proximate to a working end 104 of a surgical instrument 106 may be described. The method 200 may be carried out, for example, using a system 100 as described above in regard to FIG. 1. As illustrated in FIG. 6, the method 200 of operating the system 100 includes emitting light at a working end 104 of a surgical instrument 106 at block 202 and sensing light at the working end 104 of the surgical instrument 106 at one or more light sensors at block 204. As explained above, the light emitted may include light of at least two different wavelengths, and the sensing step may thus include sensing light of at least two different wavelengths. According to one embodiment, the light used may have wavelengths of 660 nm and 910 nm. The method 200 continues at block 206 wherein a pulsatile component is separated from a non-pulsatile component of the signal generated by the light sensor.

At block 208, one or more parameters are determined based on the pulsatile component of the signal. For example, according to the illustrated embodiment, four different parameters may be determined. First, an Eigen-derived metric may be determined that quantifies the number of principal components present in the signal and determines the dominating signal in a complex signal. Second, an autocorrelation metric may be determined that is representative of the amplitude of the autocorrelation of the detector signal at the zero$^{th}$ lag. Third, a correlation coefficient metric may be determined that quantifies the correlation coefficient between different parts of the complex signal. Fourth, a peak metric may be determined that quantifies the number of signal peaks present in the complex signal.

At block 210, the parameters are interrogated to determine if the tissue present proximate to the emitter 110/sensor 112 pair is a vessel or some other type of tissue. According to one embodiment, the interrogation may simply be whether a vessel is present proximate the working end 104 of the instrument 106. If there is a vessel present, the method 200 may proceed to block 212, and activate one or more of the output devices 130 (e.g., a "vessel present" message displayed on the display 130-2, for example). If no vessel is present, then according to this embodiment, no output device 130 is activated, although it will be recognized that an alternative output device could instead be activated or the output device 130 activated in block 212 could be activated, but a different indication provided to the user (e.g., a "no vessel" message displayed on the display 130-2, for example).

Figure 7:
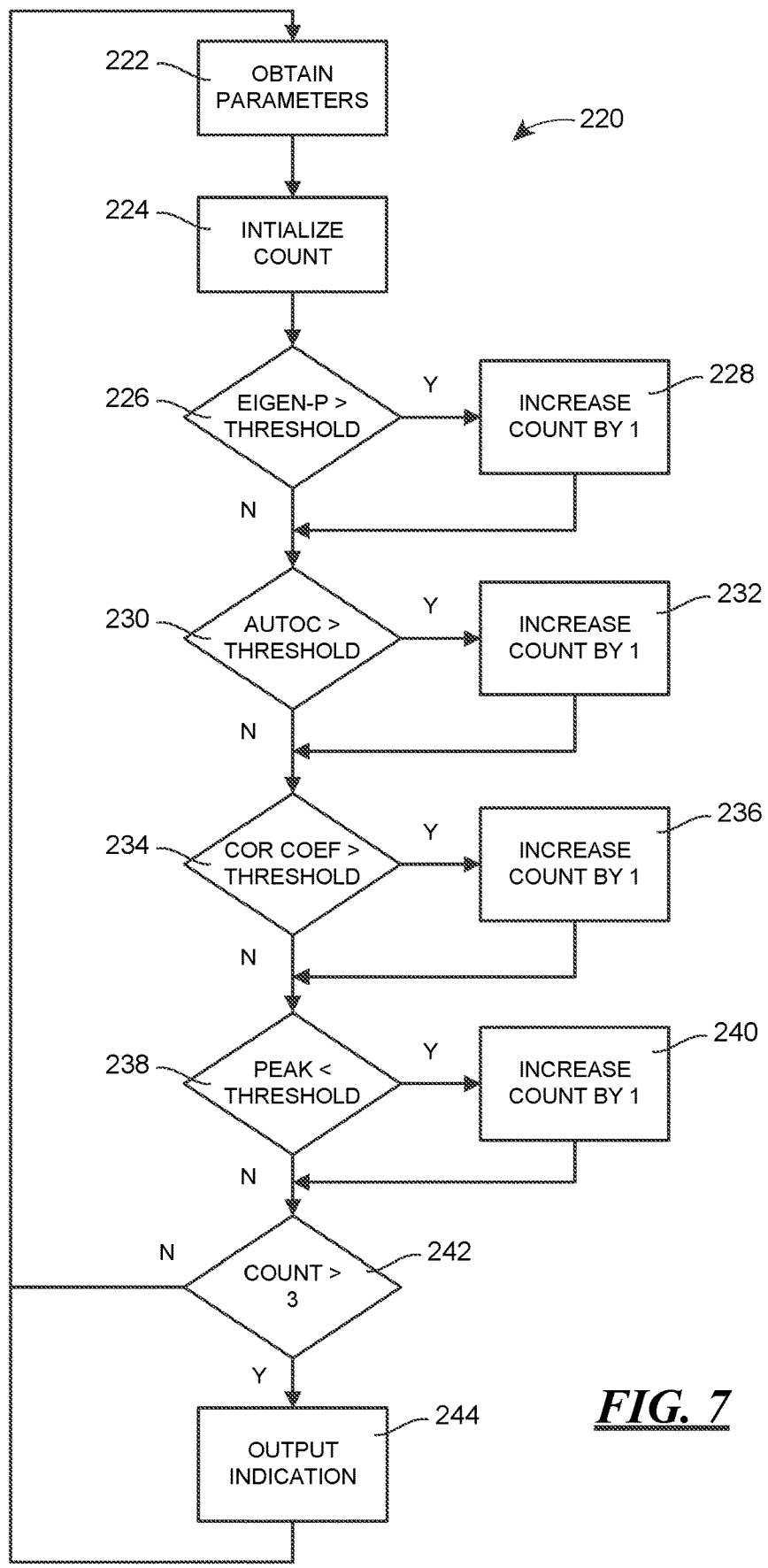
FIG. 7 is a flowchart of an embodiment of a method of determining the presence of a vessel used in the method of FIG. 6.

The specific method for carrying out the interrogation may vary, but one embodiment of a method carried out at least as part of block 210 is illustrated in FIG. 7. The method 220 of FIG. 7 begins at block 222 with the parameters having been calculated, although the method could alternatively begin with the calculation of the parameters.

As illustrated, the method 220 relies on a series of comparisons being made between the parameters and thresholds for these parameters. These thresholds may be set using empirically derived data, for example, or theoretically determined. Typically, but not necessarily, the comparison includes determining if the parameter exceeds a predetermined threshold. If at least two of the four parameters suggest that a vessel is present after comparison with the respective thresholds, then the method 220 indicates that a vessel is present proximate to the working end 104 of the instrument 106. If less than two of the parameters suggest that a vessel is present after comparison with the thresholds, then the method 220 provides no indication.

More particularly, the method 220 uses a variable, or count, to store information regarding the number of comparisons that suggest a vessel is present. Each time the method 220 determines that one of the comparisons suggests that a vessel is present, the count is increased by one. If the comparison does not suggest that a vessel is present, then the count is not increased. In a final step, the count is compared to a further threshold, defined in accordance with the aforementioned criteria (i.e., two or more favorable comparisons indicating a vessel is present, less than two indicating only tissue).

It will be recognized that the general operation of the method 220 may be varied in a number of ways. For example, a greater or lesser number of parameters may be included in the determination. In addition, the sensitivity of the comparison need not be an all-or-nothing comparison, but a range of values may be assigned based on the comparison of the calculated parameter and preexisting empirically or theoretically determined thresholds (or ranges). Further, the determination that a vessel is present could be based on at least three or more favorable comparisons, rather than at least two. Also, the use of a single variable to store the results of each comparison may be replaced by a variety of different options, such as the setting of a flag (e.g., 1/0 or T/F) for each of the comparisons, which flags are then read once all of the comparisons have been made. Other embodiments may implement further alternatives in addition to or in substitution for these enumerated options.

Returning then to the method 220 illustrated in FIG. 7, the count is initialized, for example to one, at block 224. A first comparison is made at block 226 of the Eigen-derived metric and its respective threshold. If the Eigen-derived metric exceeds the threshold, then the method 220 passes to block 228 and the count is increased by one. The method 220 then continues to block 230. If the Eigen-derived metric does not exceed the threshold, then the method 220 passes directly to block 230 and the count remains the same.

In a similar fashion, comparisons are made for the other parameters at blocks 230, 234, 238, and the count is increased at blocks 232, 236, 240 if the respective thresholds are exceeded. It will be recognized that while the comparisons made at blocks 226, 230, 234 involve determining if the parameter exceeds a threshold, the comparison made at block 238 is whether the parameter is lower than the respective threshold. It will also be recognized that the order of the comparisons made at blocks 226, 230, 234, 238 may be made in any order or even simultaneously; the order illustrated was selected simply for ease of explanation and not by way of limitation. After block 238 or block 240, the method 220 passes to block 242, where the count is compared to its respective threshold. According to the embodiment illustrated, if the count is three or greater, the method 220 provides an indication to the user that a vessel is present (e.g., via any of the output devices 130). On the other hand, if the count does not exceed three at block 242, the method 220 returns to block 222.

While the pulsatile, or AC, component is used to determine if the vessel is present or not, the DC profile may be used to adapt the intensity emitted by the light emitter 110. In particular, it is believed that the intensity of the light emitter 110 plays an important role in the accuracy of vessel detection (and potentially tissue type and/or vessel size determination). If the intensity of the light emitter 110 is set too low, too much light may be absorbed by the tissue. In such a circumstance, the sensor 112 may not be able to detect the pulsatile nature of the vessel, and it may be difficult to differentiate the vessel (e.g., artery) from the surrounding tissue (i.e., low resolution). Similar error may result if the intensity is set too high. Therefore, it would be desirable to provide a method and mechanism for selection of the intensity of the light emitter 110 that would limit the consequences of using an intensity that was either too low or too high for conditions.

For example, the amplitude of the DC component may be compared to a predetermined value, or range, and if the calculated amplitude is equal to the value or within the range, the intensity is unchanged. To the extent that the amplitude is not equal to the value or falls outside the range, then the intensity is changed, with the increase or decrease in intensity dependent upon on whether the amplitude is greater than the upper limit of the range or below the lower limit of the range, for example. According to one embodiment, the range may be empirically derived.

Figure 8:
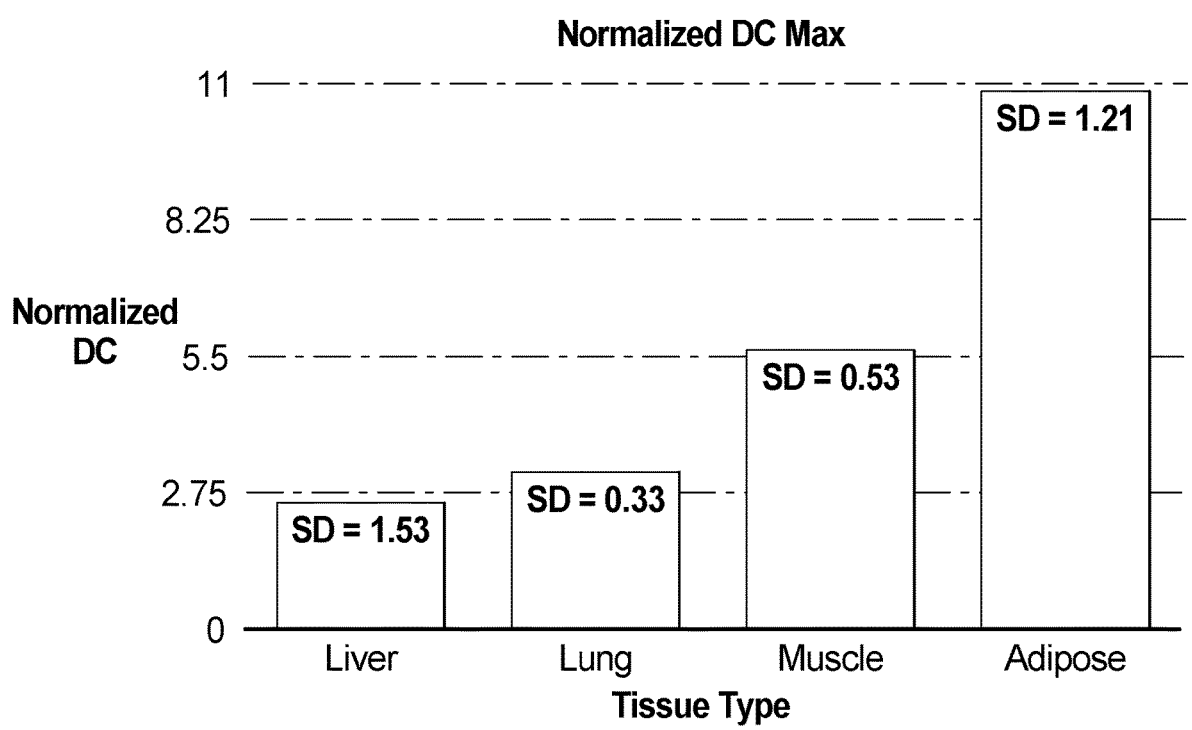
FIG. 8 is a graph of the normalized values of the non-pulsatile (DC) component of a signal generated by a light sensor for tissue-only subjects of various tissue types.

The DC component may also be used to differentiate between different types of tissue, particularly where the tissue thickness is known. That is, different tissue types scatter light to different degrees. Consequently, the DC component may be determined when either different wavelengths or different intensities of light are used, and then the DC component may be compared to a predetermined value or range to determine the tissue type present. According to one embodiment, a combination of normalized DC components in at least two wavelengths (e.g., 660 nm and 910 nm) is used to differentiate the tissue types, with more emphasis given to the wavelength in which the scattering is more dominant. For example, the ratio of the normalized DC components at the two wavelengths may be compared against a look-up table prepared using empirically derived values. According to another embodiment, a combination of multiple intensities of light of a single wavelength is used, and the rate of change of the DC component with increase light intensity is determined. FIG. 8 provides one set of normalized DC components that may be used in performing this determination, which figure is discussed in greater detail below. Even if the specific tissue type cannot be determined, the tissue type can be classified as minimally scattering (like liver or kidney tissue) or highly scattering (like muscle or adipose tissue), and such a determination or differentiation may be performed with a single wavelength (e.g., 660 nm) through comparison of the normalized DC component and the LED intensity values.

Furthermore, the DC component may be used to determine the thickness of a known type of tissue. That is, for a known tissue type and constant intensity, the thickness of the tissue present between the emitter/sensor and a vessel of interest may be calculated based on the DC component.

Having thus described the surgical system 100 and the methods 200, 220 in general terms, further details of the system 100 and its operation are provided.

Initially, while the emitter 110 and the sensor 112 are described as disposed at the working end 104 of the surgical instrument 106, it will be recognized that not all of the components that define the emitter 110 and the sensor 112 need be disposed at the working end of the instrument 106. That is, the emitter 110 may comprise a light emitting diode, and that component may be disposed at the working end 104. Alternatively, the emitter 110 may include a length of optical fiber and a light source, the source disposed remotely from the working end 104 and the fiber having a first end optically coupled to the source and a second end disposed at the working end 104. According to the present disclosure, such an emitter 110 would still be described as disposed at the working end 104 because the light is emitted in the direction of the tissue at the working end 104 of the instrument 106. A similar arrangement may be described for the sensor 112 wherein an optical fiber has a first end disposed facing the tissue and a second end optically coupled to other components that collectively define the sensor 112.

As illustrated in FIGS. 2-5, the light emitter 110 and light sensor 112 are disposed generally facing in a common direction (i.e., the direction of the tissue sample of interest). This does not require the emitter 110 and the sensor 112 to be generally disposed in a common plane (see the embodiment of FIGS. 4 and 5), although this is preferred. According to certain embodiments, the emitter 110 and sensor 112 may be formed integrally (i.e., as one piece) with jaws 180, 182 of a surgical instrument 106, although other options are possible, as discussed above. In this manner, light emitted by the emitter 110 and scattered by the tissue of interest may be captured by the light sensor 112.

Further, it is believed that the spacing between the emitter 110 and the sensor 112 may influence the light received by the sensor 112. As presently understood, after photons leave the emitter 110 in contact with tissue, an ensemble of independent photons return to the surface and reach the sensor 112. Some of the detected photons travel a short distance from the plane of the emitter and detector and exit at the site of the sensor 112, while some photons travel farther into the tissue before exiting at the surface without being absorbed (photons that are absorbed cannot contribute to the photocurrent). Path length distributions and the penetration depth of photons that reach the sensor 112 vary as a function of emitter-sensor separation, with maximum effective photon depth penetration values several times greater than the physical emitter-sensor separation. For example, it has been determined that a spacing between the emitter 110 and the sensor 112 of 5 mm may permit detection of vessels from 0 mm to 12 mm from the surface of the tissue.

Changes in blood volume, due to differences in systolic and diastolic pressures within a tissue-embedded artery, impact the relative number of long-traveling photons that survive and reach the sensor 112. The temporally observed difference in the number of long-traveling photons that results from the presence of an artery in the photon trajectory is responsible for the pulsatile (AC) signal. For a small source-detector separation, detected photons traversing the shorter distances are less exposed to the cycling blood of an artery at a greater depth below the tissue surface, and therefore survive with a more uniform likelihood between systolic and diastolic conditions. With an increased source-detector separation, a higher percentage of photons that reach the sensor 112 will be long-traveling photons, resulting in larger detected pulse amplitudes. Therefore, it is believed that increasing the spacing between the emitter 110 and the sensor 112 may permit the light to penetrate even deeper into the tissue, permitting vessel detection at even greater depths.

It is further believed that adjusting the angle of the emitter 110 and/or sensor 112 may provide a similar effect. That is, similar to the way in which a change in the linear distance between the emitter 110 and the sensor 112 allows for the sampling of a different proportion of long-traveling photons at the surface sensor 112, a variation in angle of the emitter 110 and/or sensor 112 can change the depth and the distance to which the photons travel before being sampled by the sensor 112. As a consequence, changes in the angle of the emitter and/or sensor are believed to permit the depth at which vessels can be detected by the instrument 106 to be varied.

As mentioned above, the emitter 110 and sensor 112 may be disposed so as to be mounted in a fixed relationship to each other, or a moveable or adjustable relationship.

In particular, FIG. 2 illustrates an embodiment wherein emitter 110 and sensor 112 are at a fixed spacing relative to each other, in that they are both mounted in a first jaw 180 of the instrument 106. Such an embodiment would permit the user to be confident that the vessels detected are within 12 mm from the working end 104 of the instrument 106. The emitter 110 and the sensor 112 of the embodiment of FIG. 2 also have a fixed angular relationship between the emitter 110 and the sensor 112 relative to a surface of the surgical instrument 106.

By contrast, the embodiment of FIG. 3 has the sensor 112 mounted in a first jaw 180 of the instrument 106 and the emitter 110 mounted in a second jaw 182 of the tool 106. Such an embodiment would permit the user to vary the depth of detection simply by varying the distance between the jaws 180, 182 of the instrument 106: with the jaws 180, 182 closed, the user may probe for shallow vessels (i.e., vessels disposed within 12 mm of the tissue surface), while with the jaws 180, 182 open, the user may probe for deeper vessels (i.e., vessels disposed greater than 12 mm below the tissue surface). According to the embodiment illustrated in FIG. 3, the control structure for operating the jaws 180, 182 may include a mechanism for modifying the distance between the jaws 180, 182 in a controlled fashion (e.g., in discrete increments) so that the user can determine the jaw spacing (and thus the detection depth) without visualization of the jaws 180, 182. The system 100 may provide a mechanism for determining the distance between the jaws 180, 182, which may be used in conjunction with the control structure or separate from it. In particular, for linear adjustments, the distance between the jaws 180, 182 may be measured using a potentiometer, whereby a moveable object is connected directly to a rotational shaft or slider of the potentiometer, and a reference voltage is applied across the two outer fixed connections forming the resistive element. This configuration produces a potential or voltage divider type circuit output, which is proportional to the shaft position. Once a voltage is applied across the resistive element of the potentiometer the maximum output voltage would be equal to the supply voltage, with the minimum output voltage equal to 0V. Alternatively, an absolute position rotary encoder could be used to determine the angle between the jaws 180, 182 of the instrument 106 when they are not in a parallel configuration A further alternative embodiment is illustrated in FIGS. 4 and 5. In the embodiment of FIGS. 4 and 5, the emitter 110 and the sensor 112 are each attached to a separate frame 300, 302. The frames 300, 302 are each rotatable about an axis of rotation 304, 306; while the axes of rotation 304, 306 are parallel to each other, as best seen in FIG. 5, this need not be the case according to all embodiments. In fact, the frames 300, 302 may be pivotal about more than one axis. To rotate the frames 300, 302 about the axes 304, 306, shafts 308, 310 are provided that connect the frames 300, 302 to a rotary actuator, such as a bi-directional motor 312, 314. The motor 312, 314 may be connected to a connector such that each motor 312, 314 (and thus each frame 300, 302) is adjustable independently, or such that the motors 312, 314 may be adjusted together. Similar to the embodiment of FIG. 3, a potentiometer could be included and used to determine the change in angle of either the emitter 110 or sensor 112 during operation.

The light emitter 110 may include one or more elements. According to such an embodiment, all of the elements may be adapted to emit light at a particular wavelength (e.g., 660 nm), or certain elements may emit light at different wavelengths than other elements. It is believed that a system with multiple light emitters 110 and/or multiple sensors 112 will increase the signal-to-noise ratio and the spatial resolution compared to a system containing a single emitter 110 and sensor 112.

As to those embodiments wherein the light emitter 110 is in the form of and array including one or more light emitting diodes, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 112 according to the embodiments of the present disclosure also may include one or more individual elements. As was the case with the light emitter 110, the elements of the light sensor 112 may be arranged in an array, and the discussion about the arrays above applied with equal force here.

In addition, the light sensor 112 may include a mechanism for physically excluding photons reaching the sensor 112 from a range of angles. This mechanism can consist of a mask or grated layer to physically filter any photons that are not reaching the sensor 112 at a nearly perpendicular angle. It has been observed that the mean depth penetration of the photons leaving the emitter 110 is equal to just over half the distance of source-detector separation (~2.5 mm penetration for our 5 mm spacing). This mechanism will increase the proportion of long-traveling and deep penetrating photons that are received by the sensor 112 thus increasing the depth at which the vessels can be detected by the instrument.

As discussed above, the system 100 may include hardware and software in addition to the emitter 110, sensor 112, and controller 114. For example, where more than one emitter 110 is used, a drive controller may be provided to control the switching of the individual emitter elements. In a similar fashion, a multiplexer may be provided where more than one sensor 112 is included, which multiplexer may be coupled to the sensors 112 and to an amplifier. Further, the controller 114 may include filters and analog-to-digital conversion as may be required.

As for the indicator 130 used in conjunction with controller 114, a variety of output devices may be used. As illustrated in FIG. 1, a light emitting diode 130-1 may be attached to or incorporated into the associated surgical instrument 106, and may even be disposed at the working end 104 of the instrument 106. Alternatively or in addition, an alert may be displayed on a video monitor 130-2 being used for the surgery, or may cause an image on the monitor to change color or to flash, change size or otherwise change appearance. The indicator 130 may be in the form of or include a speaker 130-3 that provides an auditory alarm. The indicator 130 also may be in the form of or may incorporate a safety lockout 130-4 associated with the surgical instrument 106 that interrupts use of the instrument 106. For example, the lockout could prevent ligation or cauterization where the surgical instrument 106 is a thermal ligature device. As a still further example, the indicator 130 also may be in the form of a haptic feedback system, such as a vibrator 130-5, which may be attached to or formed integral with a handle or handpiece of the surgical instrument 106 to provide a tactile indication or alarm. Various combinations of these particular forms of the indicator 130 may also be used.

As mentioned above, the surgical system 100 may also include the surgical instrument 106 with the working end 104, to which the light emitter 110 and light sensor 112 are attached (in the alternative, removably/reversibly or permanently/irreversibly). The light emitter 110 and the light sensor 112 may instead be formed integrally (i.e., as one piece) with the surgical instrument 106. It is further possible that the light emitter 110 and light sensor 112 be attached to a separate instrument or tool that is used in conjunction with the surgical instrument or tool 106, such as a blunt end of a dissection tool.

As noted above, the surgical instrument 106 may be a thermal ligature device in one embodiment. In another embodiment, the surgical instrument 106 may simply be a grasper or grasping forceps having opposing jaws. According to still further embodiments, the surgical instrument may be other surgical instruments such as surgical staplers, clip appliers, and robotic surgical systems, for example. According to still other embodiments, the surgical instrument may have no other function that to carry the light emitters/light sensors and to place them within a surgical field. The illustration of a single embodiment is not intended to preclude the use of the system 100 with other surgical instruments or tools 106.

Examples

Experiments have been conducted using an embodiment of the above-described system. The experiments and results are reported below.

A first set of experiments used an excised porcine carotid artery covered with porcine adipose or liver tissues of variable thickness. To simulate the pulsatile flow of fluid found in such blood vessels, a submersible DC pump was used. The pump was capable of operation at between 40 and 80 cycles per minute, and could provide a flow rate that could be set to a particular value. The fluid used was porcine whole blood to which heparin had been added and that was maintained at an elevated temperature to maintain physiological viscosity. For the experiments described below, the blood was pumped at 60 cycles per minute and at a flow rate of 500 mL per minute.

A light emitter was disposed on a common surface with a light sensor and disposed opposite the various tissue-only assemblies. The light emitter included a single light emitting diode that emitted light at 660 nm and 910 nm. The light sensor was a single element capable of detecting light at 660 nm and 910 nm. The results of the experiments are plotted in FIG. 8, where each bar represents the average normalized DC value for that given tissue type over multiple thicknesses (ranging from 2 mm to 12 mm). The standard deviation is given for samples of the same given tissue type. Highly scattering tissues (i.e., adipose and muscle) result in a higher normalized DC value than those that have lower scattering properties (i.e. liver and lung), thus allowing for the differentiation between tissue type using a combination of the LED intensity and DC output.

A second set of experiments involved a light emitter disposed on a common surface with a light sensor and disposed opposite the liver tissue-only subject or the liver tissue/excised porcine carotid artery assembly. The light emitter included a single light emitting diode that emitted light at 660 nm and 910 nm. The light sensor was a single element capable of detecting light at 660 nm and 910 nm. The results of the experiments are plotted in FIGS. 9 and 10, with the non-pulsatile component illustrated in FIG. 9 and the pulsatile component illustrated in FIG. 10.

Figure 9:
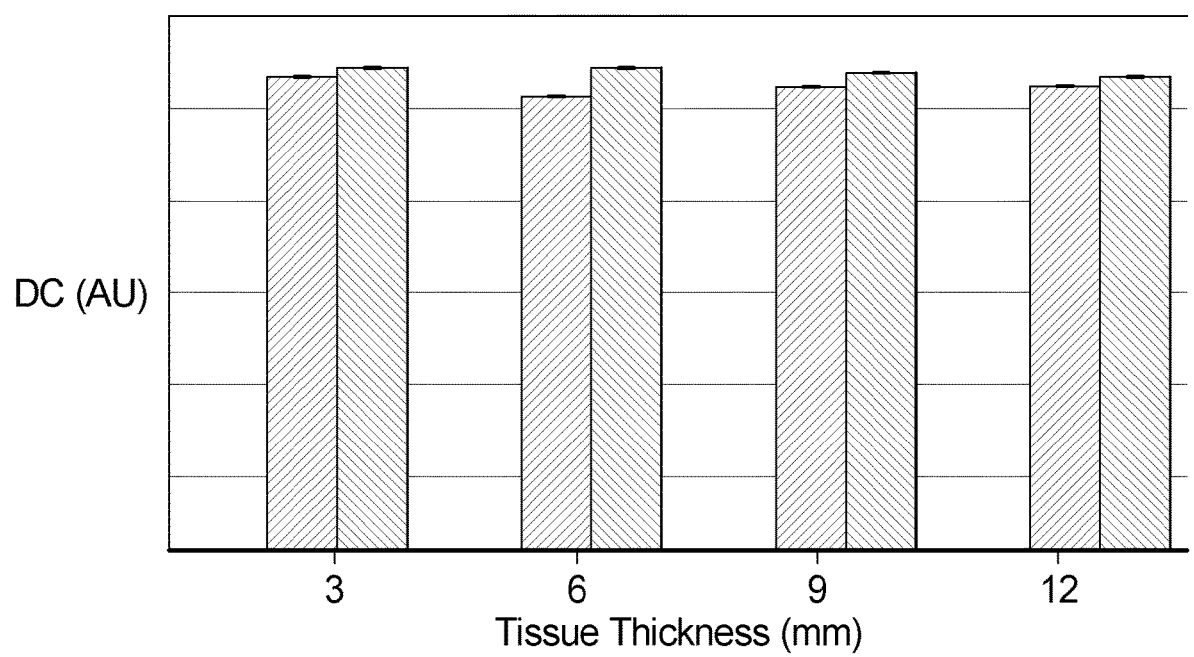
FIG. 9 is a graph of the magnitudes of the non-pulsatile (DC) component of a signal generated by a light sensor for a tissue-only subject and a tissue/vessel assembly over a range of tissue thicknesses.
Figure 10:
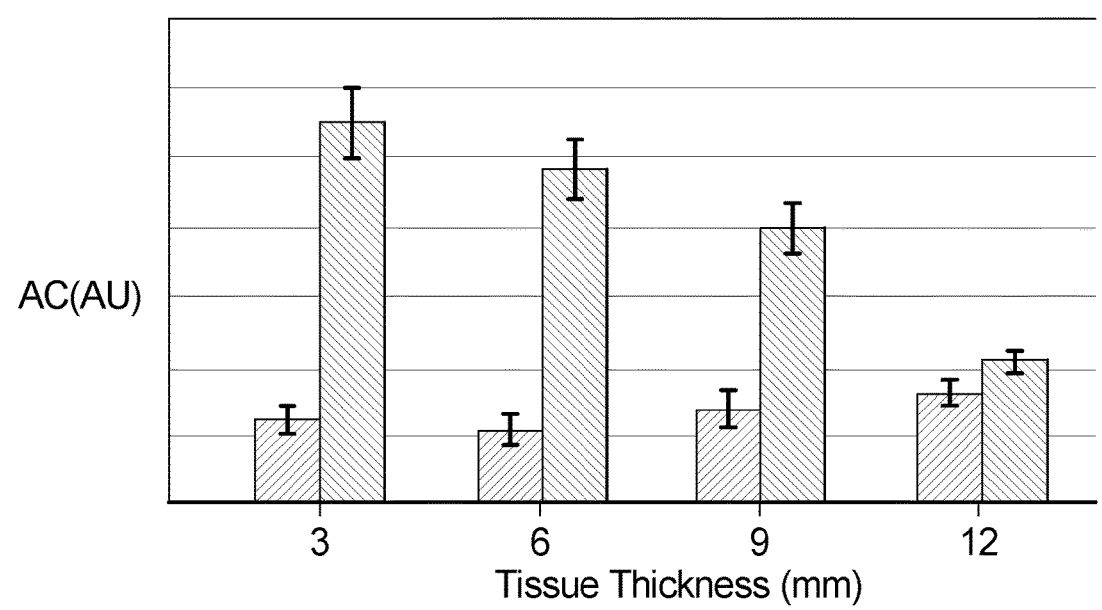
FIG. 10 is a graph of the magnitudes of the pulsatile (AC) component of a signal generated by a light sensor for a tissue-only subject and a tissue/vessel assembly over a range of tissue thicknesses.

Referring first to FIG. 9, it will be recognized that there is very little variation in the non-pulsatile component of signal representative of the reflected light received by the sensor 112 between the liver tissue-only subject (left-hand element of each pair) and the liver tissue/porcine artery assembly (right-hand element of each pair). This is generally the case regardless of the thickness of liver tissue used in the subject or assembly. Referring to FIG. 10 on the other hand, there was considerable difference in the pulsatile component between the liver tissue-only subject and the liver tissue/porcine artery assembly, with the more significant differences seen at lesser thicknesses of tissue used.

A third set of experiments used different types of tissue (i.e., adipose, liver, kidney and muscle) and excised porcine arteries. As in the previous sets of experiments, the light emitter/sensor was used with tissue-only subjects and with assemblies including a porcine artery covered with tissue. The assemblies were prepared using porcine arteries ranging in diameter from 2.5 mm to 6 mm, and covered in tissue ranging in thickness from 2 mm to 15 mm.

Figure 13:
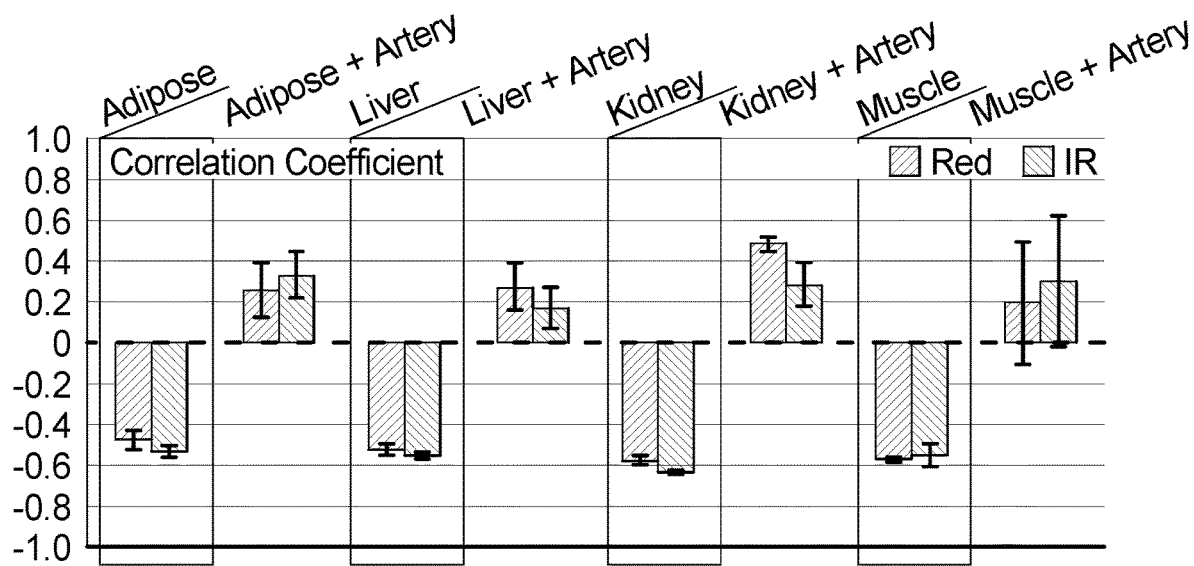
FIG. 13 is a graph of the magnitudes of a correlation coefficient metric for tissue-only subjects and tissue/vessel assemblies over a range of tissue types.
Figure 14:
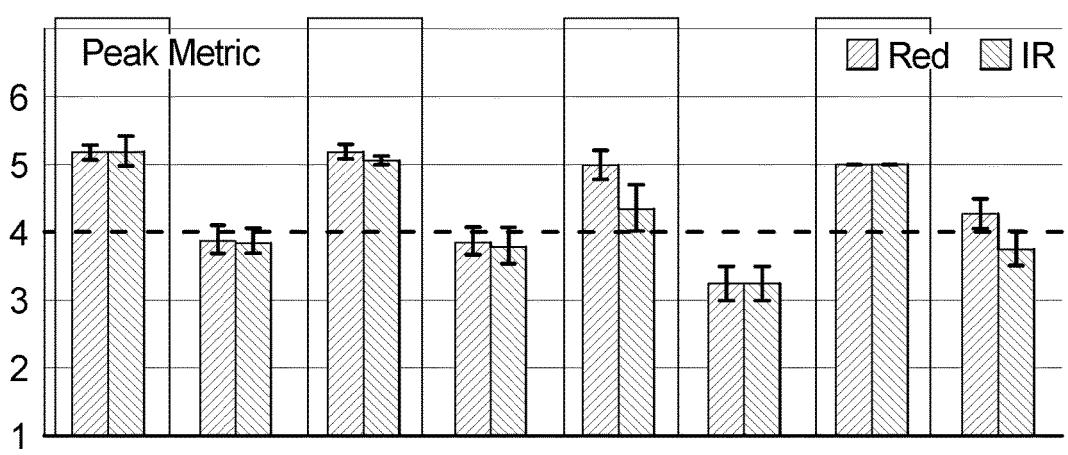
FIG. 14 is a graph of the magnitudes of a peak metric for tissue-only subjects and tissue/vessel assemblies over a range of tissue types, the subjects, assemblies and tissue types being arranged in the same order as FIG. 13.

A light emitter was disposed on a common surface with a light sensor and disposed opposite the tissue-only subject or tissue/artery assembly. The light emitter included a single light emitting diode that emitted light at 660 nm and 910 nm. The light sensor was a single element capable of detecting light at 660 nm and 910 nm. Each of the four parameters referenced above, Eigen-derived, Autocorrelation, Correlation Coefficient, and Peak, were calculated for each pair of test runs (tissue-only, tissue/artery assembly). The results of the experiments are plotted in FIGS. 11-14, with FIG. 11 including the results for the Eigen value, FIG. 12 including the results for the Autocorrelation, FIG. 13 including the results for the Correlation Coefficient, and FIG. 14 including the results for the Peak. The identification of the results relative to tissue type and subject/assembly are found in each of FIGS. 11 and 13, with FIGS. 12 and 14 following a similar order as to tissue type and subject/assembly.

In all cases, there were only minor differences between the results obtained using the light with a wavelength of 660 nm and that with a wavelength of 910 nm (in each pair, the left-hand element is the result at 660 nm, the right-hand element is the result at 910 nm). On the other hand, there was a significant difference between the results for each of the parameters calculated between the tissue-only subject and the tissue/artery assembly.

Figure 11:
FIG. 11 is a graph of the magnitudes of an Eigen-derived metric for tissue-only subjects and tissue/vessel assemblies over a range of tissue types for 660 nm or 910 nm wavelengths of emitted light.
Figure 12:
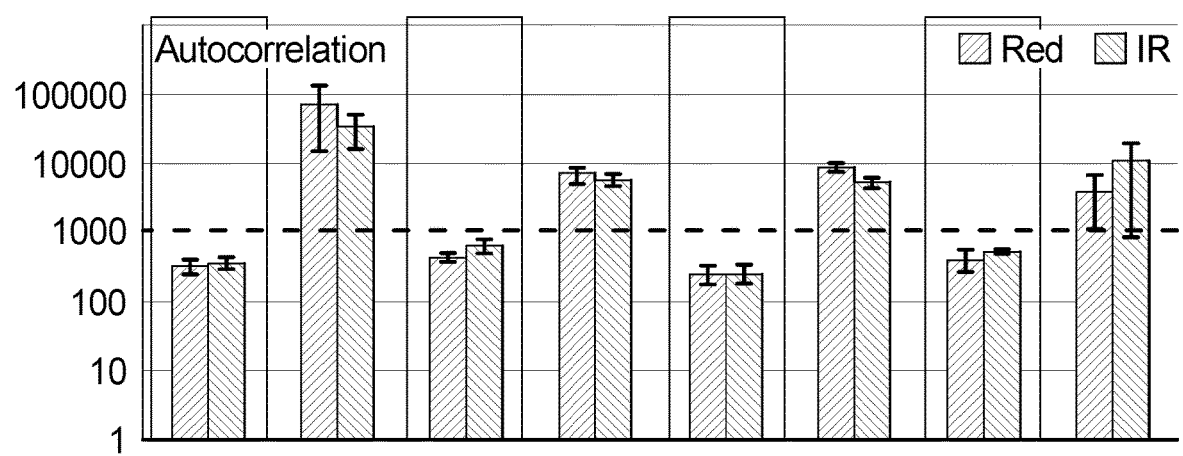
FIG. 12 is a graph of the magnitudes of an autocorrelation metric for tissue-only subjects and tissue/vessel assemblies over a range of tissue types, the subjects, assemblies and tissue types being arranged in the same order as FIG. 11.

In particular, as seen in FIG. 11, the Eigen-derived value exceeded a particular threshold (e.g., 60) for the tissue/artery assemblies, while the parameter did not exceed the threshold for the tissue-only sample. In a similar fashion, as seen in FIG. 12, the autocorrelation parameter exceeded a threshold of approximately 1000 for the tissue artery/assemblies, while the parameter did not exceed the threshold for the tissue-only sample. As to the correlation coefficient, the values were generally positive for the tissue/artery assemblies, and negative for tissue-only samples (i.e., a threshold of zero). In regard to the peak metric, all tissues types were very susceptible to noise, but the general trend illustrates a difference between the tissue-only samples and the tissue/artery assemblies at a threshold of approximately 4, with the tissue/artery assemblies having a metric that does not exceed that threshold while the metric for the tissue-only exceeds that threshold.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system configured to differentiate and identify types of tissue within a region proximate to a working end of a surgical instrument, comprising:
    at least one light emitter disposed at the working end of the surgical instrument;
    at least one light sensor disposed at the working end of the surgical instrument, facing in a common direction as the at least one light emitter, and configured to receive light emitted from the at least one light emitter and reflected from the region, the at least one light sensor configured to generate a signal comprising a first pulsatile component and a second non-pulsatile component; and
    a controller coupled to the at least one light sensor, the controller comprising a splitter configured to separate the first pulsatile component from the second non-pulsatile component and an analyzer configured to differentiate between types of nonvascular tissue within the region proximate to the working end of the surgical instrument based on the second non-pulsatile component and to determine the presence of the vessel within the region proximate to the working end of the surgical instrument based on the first pulsatile component.

2. The surgical system according to claim 1, wherein the analyzer is configured to determine the presence of the vessel according to two or more parameters determined based on the pulsatile component of the signal, the parameters comprising an Eigen-derived metric, an autocorrelation metric, a correlation coefficient metric, and a peak metric.

3. The surgical system according to claim 2, wherein the analyzer is configured to compare the one or more parameters to a threshold associated with each of the parameters, and is configured to determine that a vessel is present in the region based on at least two of the comparisons between the parameter and the associated threshold.

4. The surgical system according to claim 1, wherein the controller comprises a processor and memory, and the splitter comprises the processor programmed to separate the first pulsatile component from the second non-pulsatile component and the analyzer comprises the processor programmed to differentiate between types of nonvascular tissue within the region proximate to the working end of the surgical instrument based on the second non-pulsatile component and to determine the presence of the vessel within the region proximate to the working end of the surgical instrument based on the first pulsatile component.

5. The surgical system according to claim 1, wherein the at least one light emitter is configured to emit light of at least two different wavelengths, and the at least one light sensor is configured to detect light at the at two different wavelengths.

6. The surgical system according to claim 5, wherein the at least one light sensor is configured to detect light at 660 nm and at 910 nm.

7. The surgical system according to claim 1, wherein the controller is configured to vary an intensity of light emitted by the at least one light emitter according to an amplitude of the second non-pulsatile component.

8. The surgical system according to claim 1, further comprising a surgical instrument having first and second opposing jaw elements, the at least one light emitter disposed on the first jaw element and the at least one light sensor disposed on the second, opposing jaw element.

9. The surgical system according to claim 1, comprising first and second rotating frames, the at least one light emitter disposed on the first rotating frame and the at least one light sensor disposed on the second rotating frame.

10. The surgical system according to claim 1, wherein the analyzer is configured to differentiate between types of nonvascular tissue according to a normalized non-pulsatile component in at least two wavelengths.

11. The surgical system according to claim 10, wherein the analyzer is configured to differentiate between types of nonvascular tissue according to a ratio of the normalized non-pulsatile components in at least two wavelengths.

12. The surgical system according to claim 1, wherein the at least one light emitter is configured to emit light of a first wavelength and light of a second wavelength, and the analyzer is configured to differentiate between types of tissue according to a comparison of the non-pulsatile component of the signal generated in response to the first wavelength and the non-pulsatile component of the signal generated in response to the second wavelength.

13. The surgical system according to claim 1, wherein the analyzer is configured to determine a thickness of a known type of nonvascular tissue based on the non-pulsatile component.

14. A method of differentiate and identify types of tissue within a region proximate to a working end of a surgical instrument, comprising:
    emitting light from at least one light emitter disposed at the working end of the surgical instrument in the direction of the region;
    sensing light reflected from the region at the working end of the surgical instrument at at least one light sensor facing in a common direction as the at least one light emitter;
    generating a signal having a first pulsatile component and a second non-pulsatile component based on the light sensed at the working end of the surgical instrument;
    differentiating between types of nonvascular tissue within the region proximate to the working end of the surgical instrument based on the second non-pulsatile component; and
    determining the presence of the vessel within the region proximate to the working end of the surgical instrument based on the first pulsatile component of the signal.

15. The method according to claim 14, wherein determining the presence of the vessel comprises determining one or more parameters determined based on the pulsatile component of the signal, the parameters comprising an Eigen-derived metric, an autocorrelation metric, a correlation coefficient metric, and a peak metric.

16. The method according to claim 15, wherein determining the presence of the vessel comprises comparing the one or more parameters to a threshold associated with each of the parameters, and determining that a vessel is present in the region based on at least two of the comparisons between the parameter and the associated threshold.

17. The method according to claim 14, further comprising separating the first pulsatile component from the second non-pulsatile component.

18. The method according to claim 14, wherein emitting light comprises emitting light of at least two different wavelengths, and wherein sensing light comprises sensing light of at least two different wavelengths.

19. The method according to claim 14, further comprising varying an intensity of light emitted according to an amplitude of the second non-pulsatile component.

\* \* \* \* \*